(12) United States Patent
Chan

(10) Patent No.: US 7,618,388 B1
(45) Date of Patent: Nov. 17, 2009

(54) HIGH-RIGIDITY LIGHT-WEIGHT REHABILITATION WALKING BOOT

(76) Inventor: Shu-Chen Chan, No.260-5, Lane 58, Nanyang Rd., Fongyuan City, Taichung County (TW)

(*) Notice: Subject to any disclaimer, the term of this patent is extended or adjusted under 35 U.S.C. 154(b) by 0 days.

(21) Appl. No.: 12/242,407

(22) Filed: Sep. 30, 2008

(51) Int. Cl.
*A61F 5/00* (2006.01)

(52) U.S. Cl. .............................. 602/23; 602/27; 128/882

(58) Field of Classification Search .................. 602/5, 602/16, 23, 27; 128/882
See application file for complete search history.

(56) References Cited

U.S. PATENT DOCUMENTS

| | | | | |
|---|---|---|---|---|
| 4,974,583 A | * | 12/1990 | Freitas | 602/24 |
| 5,078,128 A | * | 1/1992 | Grim et al. | 602/23 |
| 5,176,623 A | * | 1/1993 | Stetman et al. | 602/27 |
| 5,368,551 A | * | 11/1994 | Zuckerman | 602/23 |

* cited by examiner

*Primary Examiner*—Michael A. Brown
(74) *Attorney, Agent, or Firm*—Egbert Law Offices PLLC

(57) ABSTRACT

The present invention provides a kind of high-rigidity light-weight rehabilitation walking. The boots include a foot support, two leg supports and two strengthening pieces. The foot support is made of plastics, having a bottom surface and two lateral edges. The two lateral edges are configured with slots, and there is a contact surface on top of the slots. The leg supports are made of plastics, having a stretch support, an insert and a restriction edge between the stretch support and the insert. The restriction edge can push against the contact surface on top of the slot. The strengthening pieces are buried inside the leg supports with its upper part within the range of the stretch support and its lower part within the range of the insert to strengthen the leg support structure and increase capacity of the rehabilitation walking boots to withstand side force.

7 Claims, 4 Drawing Sheets

HIGH-RIGIDITY LIGHT-WEIGHT REHABILITATION WALKING BOOT

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present invention relates generally to a kind of rehabilitation walking boot and, more particularly, to a kind of rehabilitation walking boot with a creative new structure where a strengthen piece is configured between the foot support and the leg supports to increase support rigidity.

2. Description of Related Art Including Information Disclosed Under 37 CFR 1.97 and 37 CFR 1.98

In the case of an acutely twisted ankle or broken leg, people usually need a plaster cast or splint to fix the ankle or leg. The fixture cannot be removed for a long period of medical treatment. After removal, to protect the wound and assist movement, the patient may need some support and protection products. Rehabilitation walking boots are currently widely used as support and protection products for leg rehabilitation.

The structure of rehabilitation walking boots mainly comprises a foot support and two leg supports. In conventional rehabilitation walking boots, the foot support and leg supports are linked together in a fixed form. Later, the industry developed a new type of boot, in which the foot support and leg supports are linked together in a combination form. The materials of the leg support mainly include plastics and metal. The above-mentioned rehabilitation walking boots with fixed structure usually have metal leg supports. Such leg supports have high rigidity, but the patients wearing the rehabilitation walking boots will often face the problem of heaviness and discomfort, which causes inconvenience and limitation of movement.

The above-mentioned rehabilitation walking boots can have a combination structure, usually with plastic leg supports and a foot support, which can be linked together by inserting the leg supports into the slots configured on the foot support. The plastic leg supports are light-weight and can overcome the problem of heaviness and discomfort. However, in actual application, it is found that such plastic combination-type rehabilitation walking boots may still cause a problem.

For example, in case the patient wearing the rehabilitation walking boots has a sudden fall or suffers from inappropriate external force, the leg support inserts may be easily broken, causing unexpected injury. By looking into the reasons for injury, it is found that the plastic leg support inserts are usually designed with some parts with reduced thickness and width to realize the support and limitation function. Because such parts with reduced thickness and lack width rigidity, the boots cannot withstand a strong external side force, when the patient has a sudden fall or suffers from inappropriate external force. If it is a strong side force, the insert part between the leg supports and the foot support will be easily broken due to action of the shearing force.

Thus, to overcome the aforementioned problems of the prior art, it would be an advancement in the art to provide an improved structure that can significantly improve efficacy.

Therefore, the inventor has provided the present invention of practicability after deliberate design and evaluation based on years of experience in the production, development and design of related products.

BRIEF SUMMARY OF THE INVENTION

The present invention provides a light-weight structure with both the foot support and leg supports made of plastic material, and also offer a high structural rigidity through the strengthening piece buried inside the leg supports with its upper and lower part respectively located within the ranges of the stretch support and insert of the leg supports to effectively enhance the structural rigidity of the insert part of the leg supports. Therefore, the insert part of the leg supports will have a higher capacity to withstand side force, the problem of insufficient rigidity of plastic rehabilitation walking boots being solved. Hence, the present invention can provide relevant users with a structure of rehabilitation walking boots with light weight for better wearing comfort, and high rigidity for better safety.

Although the invention has been explained in relation to its preferred embodiment, it is to be understood that many other possible modifications and variations can be made without departing from the spirit and scope of the invention as hereinafter claimed.

DETAILED DESCRIPTION OF THE INVENTION

Figure 1:
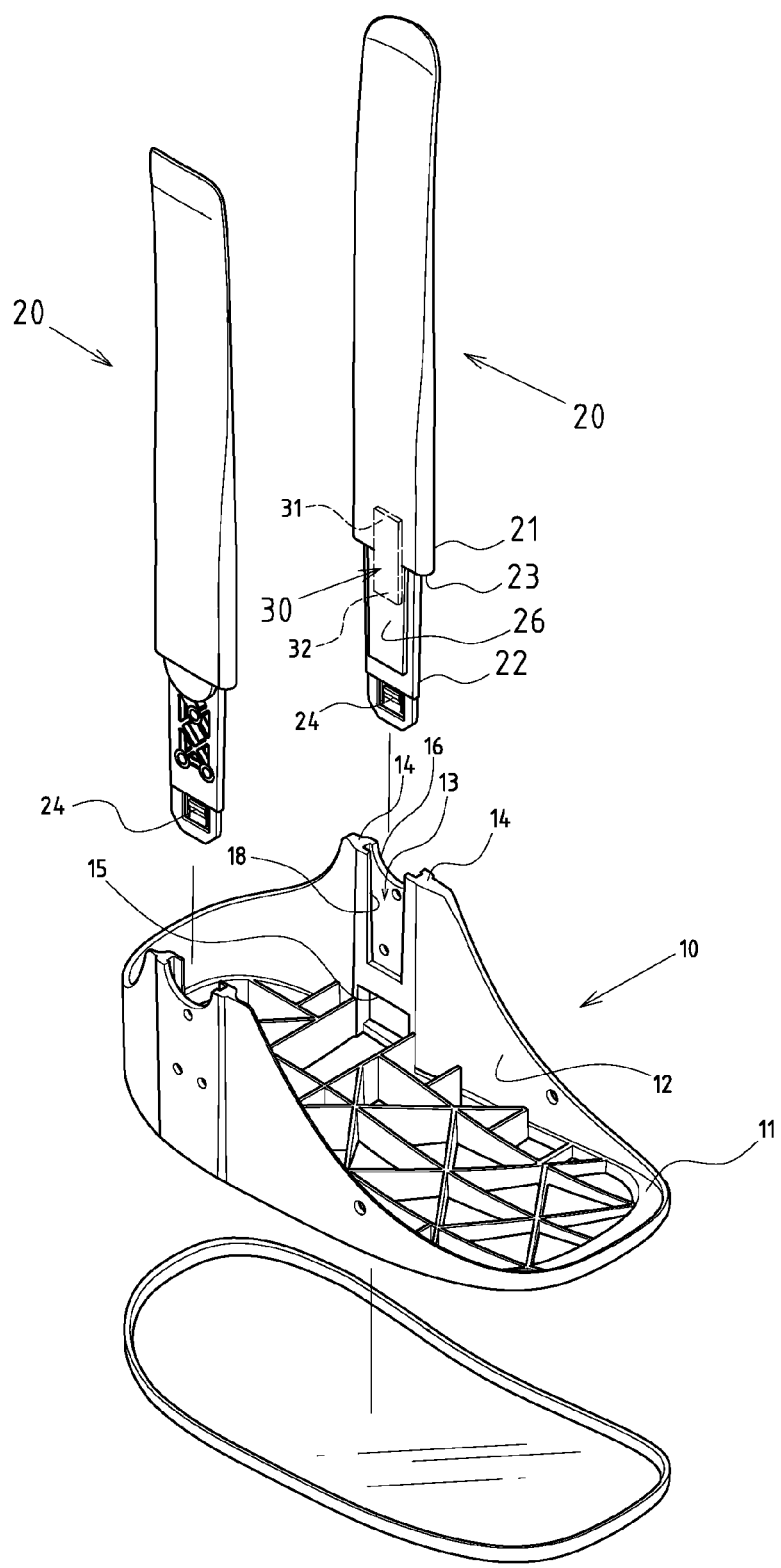
FIG. 1 shows an exploded perspective view of the present invention.
Figure 2:
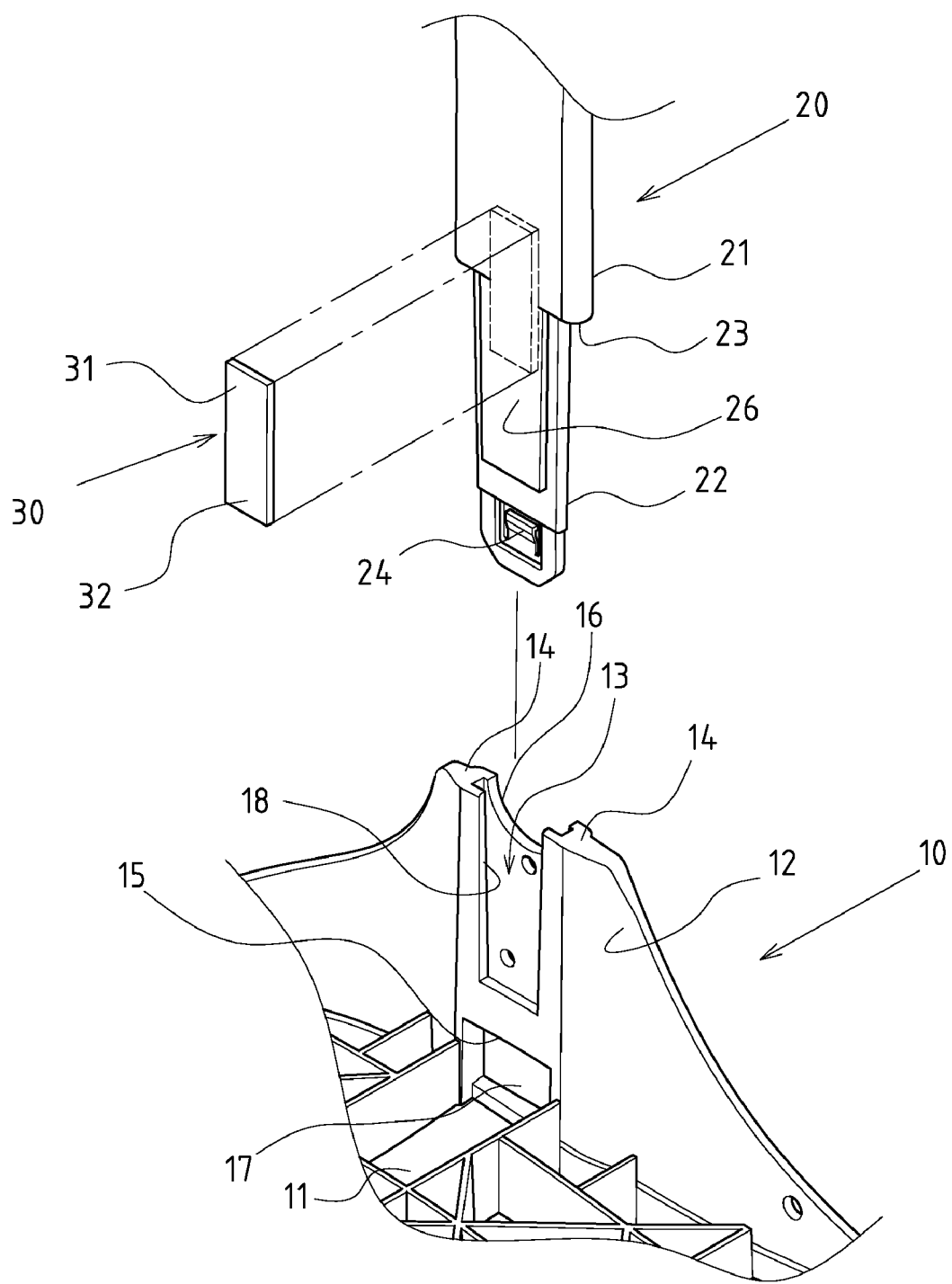
FIG. 2 shows an enlarged exploded partial perspective view of partial structure of the present invention.
Figure 3:
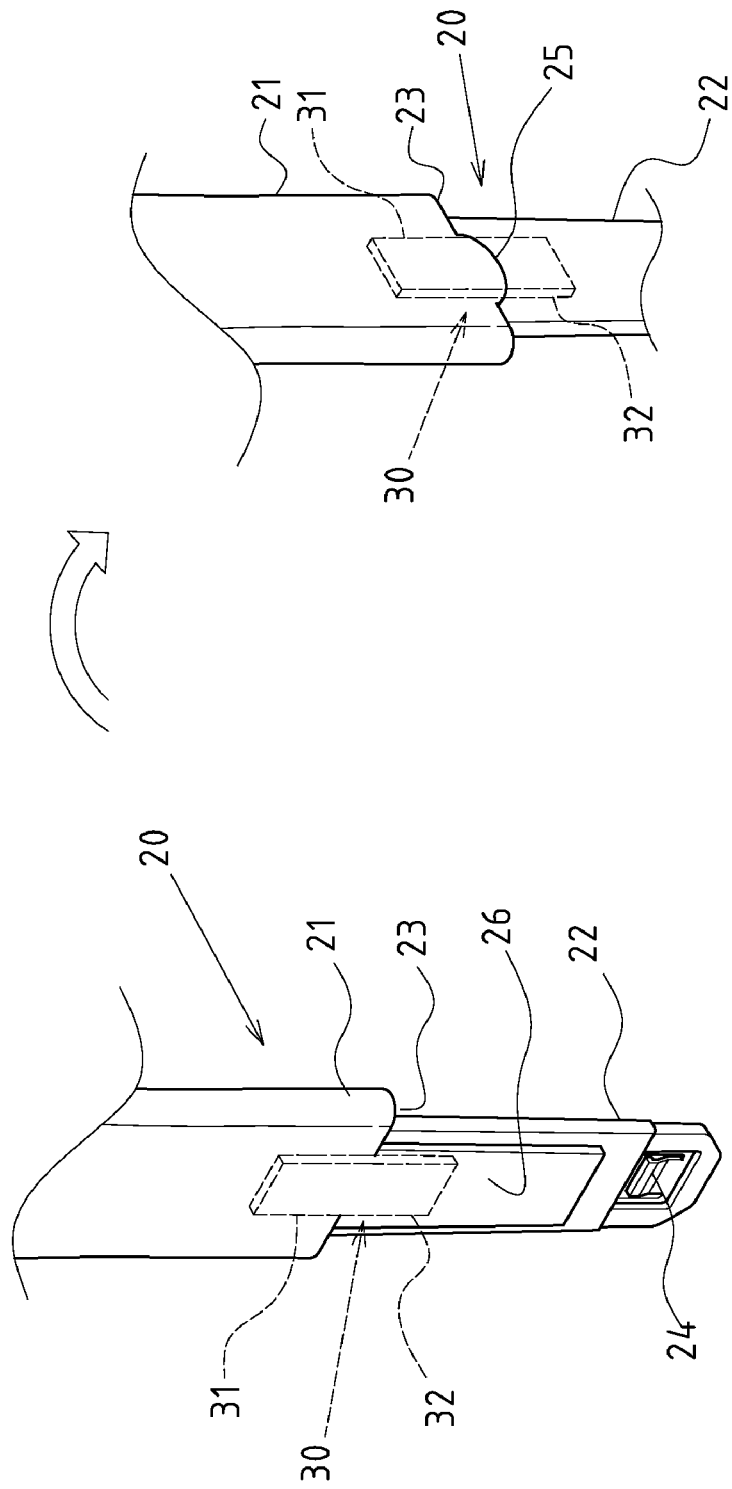
FIG. 3 shows two partial perspective parallel views of the two sides of the leg support of the present invention.
Figure 4:
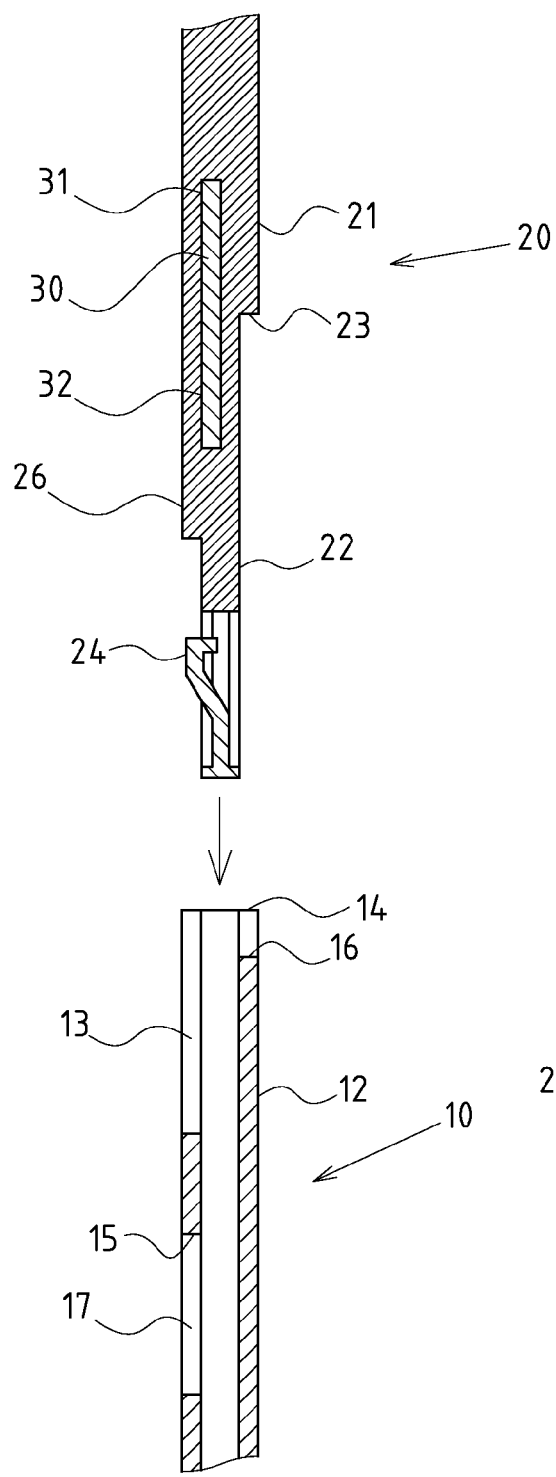
FIG. 4 shows a sectional view of the leg supports and foot support of the present invention in separate state.

The features and the advantages of the present invention will be more readily understood upon a thoughtful deliberation of the following detailed description of a preferred embodiment of the present invention with reference to the accompanying drawings.

FIGS. 1, 2, 3, 4, and 5 show the preferred embodiments of the high-rigidity light-weight rehabilitation walking boots in the present invention. However, such embodiments are presented for descriptive purposes only with respect to the claims.

The rehabilitation walking boots comprise a foot support 10, made of plastic material. The foot support 10 consists of a bottom surface 11 and two lateral edges 12, which are configured with a slot 13. On top of the slot 13, there is a contact surface 14. On one side of the slot 13, a locking part 15 is configured at a preset height. The top of the slot 13 of the foot support 10 (outside in this embodiment) can be configured with a concave edge 16, and the top of the insert 22 of the leg supports 20 can correspondingly be configured with a protrusion edge 25 (see FIG. 3). The concave edge 16 and protrusion edge 25 can be embodied in the form of matching semicircles. The halved joint between the concave edge 16 and the protrusion edge 25 can assist locking and enhance rigidity of the combination part.

Two leg supports 20 are made of plastic material, consisting of a stretch support 21, an insert 22 configured on the bottom of the stretch support 21 and a restriction edge 23 between the stretch support 21 and the insert 22. The inserts 22 can be inserted into the slots 13 configured on the lateral edges 12 of the foot support 10. The restriction edge 23 can push against the contact surface 14 on top of the slot 13. On bottom of the insert 22, there is a flexible positioning locker 24 protruding to one side, which can be aligned and locked with the locking part 15 configured on the slot 13 of said foot support 10.

Two strengthen pieces 30 are made of metal (such as steel plate), the pieces being respectively buried inside the two foot supports 10. The upper part 31 of the strengthen piece 30 is located within the range of the stretch support 21, while the lower part 32 of the strengthen piece 30 is located within the range of the insert 22.

One side of the slot 13 can be configured with a transverse rectangular perforation 17, which forms the locking part 15 through the top side wall of the slot 13. One side of the slot 13 (inner side in this embodiment) can be configured with a concave trough 18 recessing downside from the top mouth of the slot 13. And one side of the insert 22 of the leg support 20 can correspondingly be configured with a protrusion piece 26 that can just lock with the concave trough 18 to assist locking and enhance rigidity of the combination part.

Figure 5:
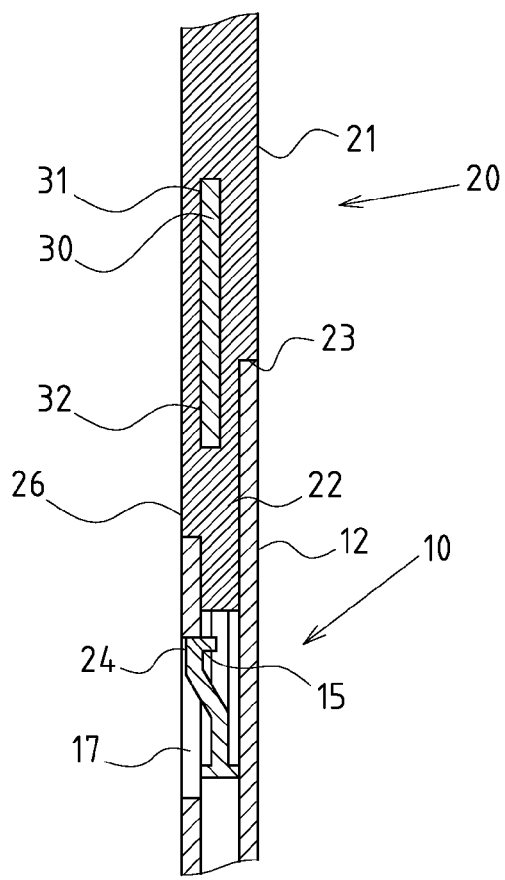
FIG. 5 shows a sectional view of the leg supports and foot support of the present invention in combined state.

FIGS. 5 and 6 show the combination of the leg supports 20 and the foot support 10 of the rehabilitation walking boots in the present invention. When the insert 22 of the leg support 20 is inserted into the slot 13 on the lateral edge 12 of the foot support 10, the flexible positioning locker 24 protruding to one side can lock with the locking part 15 on the slot 13 for positioning and fixing. On the other hand, structural design of the strengthen piece 30 buried inside the foot support 10 with its upper part 31 within the range of the stretch support 21 and its lower part 32 within the range of the insert 22 can effectively enhance the structural strength between the stretch support 21 and the insert 22 of the leg supports 20, and increase capacity of the insert part of the leg supports 20 to withstand side force.

Positions of the upper part 31 and lower part 32 of the strengthen piece 30 can be adjusted according to the structural rigidity inside the foot support 10. Also, the upper part 31 and lower part 32 of the strengthen piece 30 can be configured with equivalent or different surface areas.

I claim:

1. A walking boot of high-rigidity light-weight rehabilitation comprising:
   a foot support, being comprised of plastic material and having a bottom surface and two lateral edges each of said two lateral edges being configured with a slot, said slot having a contact surface and a locking part configured at a preset height on one side of said slot;
   two leg supports, being comprised of plastic material and having a stretch support, an insert configured on a bottom of said stretch support, and a restriction edge between said stretch support and said insert, each insert engaging into the slots configured on the lateral edges of the foot support, said restriction edge being pushed against the contact surface on top of the slot, each slot having a bottom with a flexible positioning locker protruding to one side, being aligned and locked with the locking part configured on the slot of said foot support; and
   two strengthening pieces, being comprised of metal and being respectively buried inside the leg support, each strengthening piece having an upper part located within range of the stretch support and a lower part located within range of the insert.

2. The boot defined in claim 1, wherein each strengthening piece is comprised of a steel plate.

3. The boot defined in claim 1, wherein the upper part and lower part of said strengthening piece is configured with equivalent surface areas.

4. The boot defined in claim 1, wherein the upper part and lower part of said strengthening piece is configured with different surface areas.

5. The boot defined in claim 1, wherein the top of the slot of the foot support has a concave edge, and wherein the top of the insert of the leg supports have a corresponding protrusion edge.

6. The boot defined in claim 1, wherein one side of the slot has a transverse rectangular perforation, forming the locking part through the top side wall of the slot.

7. The boot defined in claim 1, wherein one side of the slot has a concave trough recessing downward from a top mouth of the slot, and wherein one side of the insert of the leg support has a corresponding protrusion piece locked with the concave trough.

\* \* \* \* \*